United States Patent [19]
Campbell et al.

[11] Patent Number: 5,962,532
[45] Date of Patent: Oct. 5, 1999

[54] THERAPEUTIC METHOD WITH CAPSAICIN AND CAPSAICIN ANALOGUES

[76] Inventors: James N. Campbell, 707 Hillstead Dr., Lutherville, Md. 21093; Marco Pappagallo, 2809 Boston St. Aplt. 151, Baltimore, Md. 21224; Richard A. Meyer, 10084 Shaker Dr., Columbia, Md. 21046

[21] Appl. No.: 09/041,294

[22] Filed: Mar. 12, 1998

Related U.S. Application Data

[60] Provisional application No. 60/040,697, Mar. 13, 1997.

[51] Int. Cl.$^6$ ..................................................... A61L 31/16
[52] U.S. Cl. ............................................................ 514/627
[58] Field of Search .............................................. 514/627

[56] References Cited

U.S. PATENT DOCUMENTS

| | | |
|---|---|---|
| 4,424,205 | 1/1984 | LaHann et al. . |
| 4,812,446 | 3/1989 | Brand . |
| 4,997,853 | 3/1991 | Bernstein ................................ 514/626 |
| 5,008,289 | 4/1991 | Bernstein ................................ 514/535 |
| 5,188,837 | 2/1993 | Domb . |
| 5,290,816 | 3/1994 | Blumberg . |
| 5,762,963 | 6/1998 | Byas-Smith ............................. 424/472 |

FOREIGN PATENT DOCUMENTS

WO 96/40079    12/1996    WIPO .

OTHER PUBLICATIONS

Haynes, et al., "Ultra-long-duration Local Anesthesia Produced by Injection of Lecithin-coated Methoxyflurane Microdroplets," *Anesthesiology* 63:490–499 (1985).

Masters, et al., "Prolonged Sciatic Nerve Blockade Using Sustained Release of Veratridine from a Biodegradable Polymer Matrix, " *Soc. Neurosci. Abstr.* 18(1):200 Abstract No. 94.3 (1992).

Schneider, et al., "A Preferential Inhibition of Impulses in C-fibers of the Rabbit Vagus Nerve by Veratridine, an Activator of Sodium Channels," *Anesthesiology* 74:270–280 (1991).

Toh, et al., "The Pharmacological Actions of Capsaicin and Analogues," *Brit. J. Pharm.* 10:175–182 (1955).

*Primary Examiner*—William R. A. Jarms
*Attorney, Agent, or Firm*—Arnall Golden & Gregory, LLP

[57] ABSTRACT

Methods and compositions for treating pain at a specific site with an effective concentration of capsaicin or analogues thereof are described. The methods involve providing anesthesia to the site where the capsaicin or analogues thereof is to be administered, and then administering an effective concentration of capsaicin to the joint. The anesthesia can be provided directly to the site, or at remote site that causes anesthesia at the site where the capsaicin is to be administered. For example, epidural regional anesthesia can be provided to patients to which the capsaicin is to be administered at a site located from the waist down. By pretreating the site with the anesthetic, a significantly higher concentration of capsaicin can be used. Effective concentrations of capsaicin or analogues thereof range from between 0.01 and 10% by weight, preferably between 1 and 7.5% by weight, and more preferably, about 5% by weight. This provides for greater and more prolonged pain relief, for periods of time ranging from one week to several weeks. In some cases the pain relief may be more sustained because the disease that underlies the pain may improve due to a variety of factors including enhancement of physical therapy due to less pain in the soft tissues which may foster enhanced mobilization of soft tissues, tendons, and joints.

25 Claims, No Drawings

THERAPEUTIC METHOD WITH CAPSAICIN AND CAPSAICIN ANALOGUES

This application claims priority to U.S. Ser. No. 60/040,697 entitled "Therapeutic Method with Capsaicin and Capsaicin Analogues" filed Mar. 13, 1997 by James N. Campbell.

FIELD OF THE INVENTION

This application is directed to compositions and methods for relieving pain at a specific site, for example, associated with inflammation of joints, tendons, nerves, muscle, and other soft tissues, nerve injury and neuropathies, and pain from tumors in soft tissues or bone.

BACKGROUND OF THE INVENTION

Capsaicin, a pungent substance derived from the plants of the solanaceae family (hot chili peppers) has long been used as an experimental tool because of its selective action on the small diameter afferent nerve fibers (C fibers and A-delta fibers) that are believed to signal pain. From studies in animals, capsaicin appears to trigger C fiber membrane depolarization by opening cation channels permeable to calcium and sodium. Recently one of the receptors for capsaicin effects has been cloned.

Although detailed mechanisms are not yet known, capsaicin mediated effects include: (i) activation of nociceptors in peripheral tissues; (ii) eventual desensitization of peripheral nociceptors to one or more stimulus modalities; (iii) cellular degeneration of sensitive A-delta and C fiber afferents; (iv) activation of neuronal proteases; (v) blockage of axonal transport; and (vi) the decrease of the absolute number of nociceptive fibers without affecting the number of non-nociceptive fibers.

Because of capsaicin's ability to desensitize nociceptors in peripheral tissues, its potential analgesic effects have been assessed in various clinical trials. However, since the application of capsaicin itself frequently causes burning pain and hyperalgesia apart from the neuropathic pain being treated, patient compliance has been poor and the drop out rates during clinical trials have exceeded fifty percent. The spontaneous burning pain and hyperalgesia are believed to be due to intense activation and temporary sensitization of the peripheral nociceptors at the site of capsaicin application. This activation and sensitization occur prior to the desensitization phase. The activation phase could be a barrier to use of capsaicin because of the pain produced.

It would be advantageous to provide methods and compositions including capsaicin or analogues thereof with effective concentrations to cause an analgesic effect without the side effects normally associated with the use of capsaicin.

It is therefore an object of the present invention to provide a method for using capsaicin or capsaicin analogues at high concentrations with a prolonged effect.

SUMMARY OF THE INVENTION

Methods and compositions for treating pain at a specific site with an effective concentration of capsaicin or analogues thereof are described. The methods involve providing anesthesia to the site where the capsaicin or analogues thereof is to be administered, and then administering an effective concentration of capsaicin to the joint site. The anesthesia can be provided directly to the site, or at remote site that causes anesthesia at the site where the capsaicin is to be administered. For example, epidural regional anesthesia can be provided to patients to which the capsaicin is to be administered at a site located from the waist down. By pretreating the site with the anesthetic, a significantly higher concentration of capsaicin can be used. Effective concentrations of capsaicin or analogues thereof range from between 0.01 and 10% by weight, preferably between 1 and 7.5% by weight, and more preferably, about 5% by weight. This provides for greater and more prolonged pain relief, for periods of time ranging from one week to several weeks. In some cases the pain relief may be more sustained because the disease that underlies the pain may improve due to a variety of factors including enhancement of physical therapy due to less pain in the soft tissues which may foster enhanced mobilization of soft tissues, tendons, and joints.

DETAILED DESCRIPTION OF THE INVENTION

The methods and compositions described herein can be used to provide prolonged and enhanced pain relief at a specific site or sites. There are two major aspects to the methods: providing anesthesia at the site where the pain is to be relieved, then providing an effective concentration of capsaicin at the site where the pain is to be relieved, either by direct administration to the site or administration to an adjacent site allowing for delivery or passage of the capsaicin to the site to be treated.

Examples of conditions to be treated include pain from nerve injury (neuromas and neuromas in continuity), neuropathies, pain from tendenitis, myalgias (pain originating from disease and/or inflammation of muscle), bone or joint pain associated with inflammation or caused by injury or arthritis associated with degenerative diseases, rheumatoid arthritis, and other arthritic conditions, pain associated with painful trigger points, and pain from tumors in soft tissues.

Anesthesia

Anesthesia is provided so that there is relief from pain at the site where the capsaicin is administered and/or needed. Anesthesia can be administered directly, for example, by local administration of an anesthetic such as lidocaine or bupivacaine, or at a distant location, such as by a somatic or neuraxial block.

As used herein, the term "local anesthetic" means a drug which provides local numbness or pain relief. A number of different local anesthetics can be used, including dibucaine, bupivacaine, ropivacaine, etidocaine, tetracaine, procaine, chlorocaine, prilocaine, mepivacaine, lidocaine, xylocaine, 2-chloroprocaine, and acid addition salts or mixtures thereof. 2-chloroprocaine hydrochloride may be preferred due to its short action. In some embodiments, general anesthetic can be given as well.

Delivery systems can also be used to administer local anesthetics that produce modality-specific blockade, as reported by Schneider, et al., *Anesthesiology*, 74:270–281 (1991), or that possess physical-chemical attributes that make them more useful for sustained release then for single injection blockade, as reported by Masters, et al., *Soc. Neurosci. Abstr.*, 18:200 (1992), the teachings of which are incorporated herein. An example of a delivery system include microspheres wherein the anesthetic is incorporated into the polymer in a percent loading of 0.1% to 90% by weight, preferably 5% to 75% by weight. It is possible to tailor a system to deliver a specified loading and subsequent maintenance dose by manipulating the percent drug incorporated in the polymer and the shape of the matrix, in addition to the form of local anesthetic (free base versus salt)

and the method of production. The amount of drug released per day increases proportionately with the percentage of drug incorporated into the matrix (for example, from 5 to 10 to 20%). Other forms of the polymers include microcapsules, slabs, beads, and pellets, which in some cases can also be formulated into a paste or suspension.

The delivery systems are most preferably formed of a synthetic biodegradable polymer, although other materials may also be used to formulate the delivery systems, including proteins, polysaccharides, and non-biodegradable synthetic polymers. It is most preferable that the polymer degrade in vivo over a period of less than a year, with at least 50% of the polymer degrading within six months or less. Even more preferably, the polymer will degrade significantly within a month, with at least 50% of the polymer degrading into non-toxic residues which are removed by the body, and 100% of the anesthetic and glucocorticoid being released within a two week period. Polymers should also preferably degrade by hydrolysis by surface erosion, rather than by bulk erosion, so that release is not only sustained but also linear. Polymers which meet this criteria include some of the polyanhydrides, poly(hydroxy acids) such as co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other polymers include protein polymers such as gelatin and fibrin and polysaccharides such as hyaluronic acid. Polylactic acid is not useful since it takes at least one year to degrade in vivo. The polymers should be biocompatible. Biocompatibility is enhanced by recrystallization of either the monomers forming the polymer and/or the polymer using standard techniques.

Other local carrier or release systems can also be used, for example, the lecithin microdroplets or liposomes of Haynes, et al., *Anesthesiology* 63, 490–499 (1985), or the polymer-phospholipid microparticles of U.S. Pat. No. 5,188,837 to Domb.

Methods for manufacture of suitable delivery systems for administration of the local anesthetic are known to those skilled in the art. The formulations may also be designed to deliver both the anesthetic and the capsaicin, either simultaneously or sequentially.

Capsaicin Compositions

Suitable capsaicin compositions include capsaicin (trans 8-methyl-N-vanillyl-6-noneamide) or analogues thereof in a concentration between about 0.01 and 10% by weight, preferably between 1 and 7.5% by weight, and more preferably, about 5% by weight, to effectuate prolonged relief.

As used herein, the terms "capsaicin" and "capsaicin-like compound" include capsaicin and capsaicin analogues, unless otherwise specified. Analogues of capsaicin with similar physiological properties, i.e., triggering C fiber membrane depolarization by opening of cation channels permeable to calcium and sodium, are known. For example, reinsiferatoxin is described as a capsaicin analogue in U.S. Pat. No. 5,290,816 to Blumberg. U.S. Pat. No. 4,812,446 to Brand (Procter & Gamble Co.) describes other capsaicin analogues and methods for their preparation. U.S. Pat. No. 4,424,205 cites capsaicin-like analogues. Ton et al., Brit. J. Pharm. 10:175–182 (1955) discusses the pharmacological actions of capsaicin and its analogues.

Useful capsaicin compositions can be prepared by mixing capsaicin or analogues thereof to a desired concentration by weight, in a pharmaceutically acceptable carrier for intra-articular vide supra administration (e.g. administration to a joint site). Such carriers are well known to those of skill in the art, and include saline and phosphate buffered saline.

Where a capsaicin analogue is selected to replace some or all of the capsaicin, the analogue can be selected from those analogues with similar physiological properties to capsaicin as are known in the art. Compositions including such a high concentration of capsaicin or analogues thereof should be handled with care.

Methods of Treatment

The anesthetic is administered in the preferred embodiment by direct injection to the site where the capsaicin is to be administered, for example, by injection of the capsaicin analogue directly in the diseased or pain producing structure or the injured nerve or the nerve that provides innervation to the painful area, or to effect a regional block of the area including the site where the capsaicin is to be administered. In the embodiment wherein the anesthetic is administered as microspheres, the microspheres may be injected through a trochar, or the pellets or slabs may be surgically placed adjacent to nerves, prior to surgery or following repair or washing of a wound. The microspheres can be administered alone when they include both the capsaicin and local anesthetic or in combination with a solution including capsaicin in an amount effective to prolong nerve blockade by the anesthetic released from the microspheres. The suspensions, pastes, beads, and microparticles will typically include a pharmaceutically acceptable liquid carrier for administration to a patient, for example, sterile saline, sterile water, phosphate buffered saline, or other common carriers.

Preferred methods of administering the anesthetic include injection of the anesthetic into the epidural space adjacent to the spine for pain originating below a patient's waist, or directly into a joint for pain originating above the patient's waist. The prior administration of a proximal neural block sufficiently desensitizes C fibers to the expected pungent side effects of the subsequent capsaicin administration.

The expected side effects of the high dose application of the capsaicin composition are believed to be from the intense nociceptor discharge occurring during the excitatory phase before nociceptor desensitization. However, the prior administration of an anesthetic vide supra such as a nerve block, proximally or directly to the site of administration, eliminates or substantially reduces such side effects. If some "breakthrough pain" occurs despite the anesthetic, this pain may be treated by administering an analgesic such as a narcotic analgesic (i.e., the various alkaloids of opium, such as morphine, morphine salts, and morphine analogues such as normorphine). The administration of the capsaicin composition can be repeated if necessary. Suitable injection volumes of capsaicin compositions to be delivered range from between about 0.1 and 20 ccs, depending on the site to be treated.

The administration of the anesthetic along with the subsequent administration of capsaicin alleviates pain at the site for a prolonged period of time. Patients can be monitored for pain relief and increased movement, in the situation where treatment is in a joint. The treatment can be repeated as necessary to control the symptoms.

Those skilled in the art will recognize, or be able to ascertain using no more than routine experimentation, many equivalents to the specific embodiments to the methods described herein. Such equivalents are intended to be encompassed by the following claims. The references cited herein are hereby incorporated by reference.

We claim:

1. A method for providing relief from pain at a specific site in a patient in need of treatment thereof comprising:
   a) administering to the patient an effective amount of an anesthetic to alleviate the pain associated with injection of capsaicin to the painful site which results from the intense nociceptor discharge occurring during the excitatory phase following injection of the capsaicin, and
   b) injecting into the site capsaicin or capsaicin analogue in a dosage formulation having a concentration between about 0.01 and 10% by weight capsaicin, wherein the dosage is effective to prevent pain at the site.

2. The method of claim 1, wherein the concentration of the capsaicin is between 1 and 7.5% by weight.

3. The method of claim 2, wherein the concentration of the capsaicin is about 5% by weight.

4. The method of claim 1, wherein the pain results from nerve injury or neuropathies.

5. The method of claim 1 wherein the pain results from tendonitis, myalgias (pain originating from disease and/or inflammation of muscle), or bone or joint pain associated with inflammation or caused by injury or arritis associated with degenerative diseases, rheumatoid arthritis, or other arthritic conditions.

6. The method of claim 1 wherein the pain is associated with painful trigger points.

7. The method of claim 1 wherein the pain is from tumors in soft tissues.

8. The method of claim 1, wherein the anesthetic is administered as a proximal, regional, somatic, or neuraxial block.

9. The method of claim 1, wherein the anesthetic is administered directly to the site.

10. The method of claim 1, further comprising administering a narcotic analgesic to further inhibit the irritant effects of the capsaicin.

11. A kit for treatment of pain comprising:
   a) capsaicin or capsaicin analogues in a pharmaceutically acceptable formulation for injection in a patient at a painful site, in a dosage amount effective to alleviate the pain;
   b) an anesthetic in a pharmaceutically acceptable carrier for administration to a patient in an amount effective to alleviate the pain resulting from the intense nociceptor discharge occurring as a result of the injection of the capsaicin; and
   c) means for injection of the capsaicin into the painful site.

12. The kit of claim 11 wherein the anesthetic is a local anesthetic.

13. The kit of claim 11 wherein the anesthetic is a general anesthetic.

14. The kit of claim 11 further comprising delivery means for the anesthetic wherein the anesthetic is formulated to effect a proximal, regional, somatic, or neuraxial block.

15. The kit of claim 11 wherein the anesthetic and capsaicin are formulated together.

16. The kit of claim 11 wherein the anesthetic is provided in a controlled release formulation.

17. The method of claim 1 wherein the anesthetic is a narcotic anesthetic.

18. The method of claim 1 wherein the capsaicin analogue is reinsiferatoxin.

19. The method of claim 1 wherein the anesthetic is administered as a local anesthetic.

20. The method of claim 1 wherein the anesthetic is administered as a general anesthetic.

21. The method of claim 1 wherein the anesthetic is administered as a spinal block.

22. The method of claim 1 wherein the anesthetic is administered as an epidural block.

23. The method of claim 1 wherein the anesthetic is administered as a nerve block.

24. The kit of claim 11 wherein the anesthetic is a narcotic anesthetic.

25. The kit of claim 11 wherein the capsaicin analogue is reinsiferatoxin.

* * * * *